US012746250B2

(12) United States Patent
Weiss et al.

(10) Patent No.: US 12,746,250 B2
(45) Date of Patent: Sep. 29, 2026

(54) **HUMAN MILK OLIGOSACCHARIDES FOR IMPROVING RESISTANCE OF ORGANISM AGAINST *STAPHYLOCOCCUS AUREUS* INFECTION**

(71) Applicants: Inner Mongolia Yili Industrial Group Co., Ltd., Hohhot City (CN); INNER MONGOLIA DAIRY TECH RES INSTITUTE CO LTD, Hohhot City (CN)

(72) Inventors: Gisela Adrienne Weiss, Hohhot City (CN); Carolien Annika Van Loo-Bouwman, Hohhot City (CN); Gerrit Smit, Hohhot City (CN); Wendan Wang, Hohhot City (CN); Ignatius Man-Yau Szeto, Hohhot City (CN); Fangjie Gu, Hohhot City (CN); Biao Liu, Hohhot City (CN)

(73) Assignees: Inner Mongolia Yili Industrial Group Co., Ltd., Hohhot City (CN); Inner Mongolia Dairy Tech Res Institute Co Ltd, Hohhot City (CN)

( * ) Notice: Subject to any disclaimer, the term of this patent is extended or adjusted under 35 U.S.C. 154(b) by 85 days.

(21) Appl. No.: 17/995,228

(22) PCT Filed: Apr. 6, 2021

(86) PCT No.: PCT/CN2021/085623
§ 371 (c)(1),
(2) Date: Sep. 30, 2022

(87) PCT Pub. No.: WO2021/197492
PCT Pub. Date: Oct. 7, 2021

(65) Prior Publication Data
US 2023/0149432 A1 May 18, 2023

(51) Int. Cl.
*A61K 31/702* (2006.01)
*A23C 9/152* (2006.01)
*A23L 33/21* (2016.01)
*A61P 31/04* (2006.01)

(52) U.S. Cl.
CPC ............ *A61K 31/702* (2013.01); *A23C 9/152* (2013.01); *A23L 33/21* (2016.08); *A61P 31/04* (2018.01)

(58) Field of Classification Search
CPC .............................. A61K 31/702; A23L 33/40
See application file for complete search history.

(56) References Cited

U.S. PATENT DOCUMENTS

2009/0162323 A1 6/2009 Boehm et al.
2010/0260720 A1 10/2010 Sprenger
2012/0294840 A1 11/2012 Newburg et al.
2015/0265661 A1 9/2015 Newburg et al.
2018/0042950 A1* 2/2018 Davis ................ A61K 31/7016
2019/0160082 A1 5/2019 Berger et al.
2019/0224254 A1 7/2019 Kyle et al.

FOREIGN PATENT DOCUMENTS

CN 101330837 A 12/2008
CN 10190644 A 12/2010
CN 101909644 A 12/2010
CN 104507483 A 4/2015
CN 109043542 A 12/2018
NZ 771554 A 3/2024
WO 2012158517 A1 11/2012
WO 2015157098 A1 10/2015
WO 2016106198 A1 6/2016
WO 2017035412 A1 3/2017
WO 2018155995 A1 8/2018
WO WO-2019101489 A1 * 5/2019 .............. C12P 19/26
WO 2019090180 A1 8/2019

OTHER PUBLICATIONS

Ackerman, D. et al., ACS Infectious Diseases, "Antimicrobial and Antibiofilm Activity of Human Milk Oligosaccharides against *Streptococcus agalactiae, Staphylococcus aureus*, and Acinetobacter baumannii", 2018, vol. 4, pp. 315-324 (Year: 2018).*
Hunt, K. M. et al., Applied and Environmental Microbiology, "Human Milk Oligosaccharides Promote the Growth of Staphyloccci", 2012, vol. 78, No. 14, pp. 4763-4770 (Year: 2012).*
Wang, W-L., et al., "Comparison of anti-pathogenic activities of the human and bovine milk N-glycome: Fucosylation is a key factor", Food Chemistry 235 (2017) 167-174.
International Search Report for International Application No. PCT /CN2021/085623, Breast Milk Oligosaccharides for Improving Resistance of Organism Against *Staphylococcus aureus* Infection, date of mailing: Jun. 29, 2021.
Chinese Search Report for Chinese Application No. 2021103663073, "Breast milk oligosaccharide capable of Improving resistance of organism to *Staphylococcus aureus* infection" dated Nov. 15, 2022.
Search report issued on Nov. 29, 2025 for counterpart Chinese patent application No. 202410486235.X, along with machine EN translation downloaded from EPO.

(Continued)

*Primary Examiner* — Bahar Craigo
(74) *Attorney, Agent, or Firm* — Hamilton, Brook, Smith & Reynolds, P.C.

(57) ABSTRACT

The present invention relates to the field of food and pharmaceutical products, and specifically to human milk oligosaccharide for improving resistance of organism against *Staphylococcus aureus* infection. In particular, the present invention relates to use of human milk oligosaccharide in preparation of a nutritional composition or medicament for prevention and/or treatment of diseases associated with *Staphylococcus aureus* infection in individuals, or for alleviation of discomfort associated with *Staphylococcus aureus* infection, or for improvement of an individual's resistance against *Staphylococcus aureus* infection, or for improvement of an individual's innate immunity and/or anti-aging.

2 Claims, 9 Drawing Sheets

(56) References Cited

OTHER PUBLICATIONS

Wei, Jianfeng, A write in scientific papers and literature search, Waishidi, Oxford Scientific Technical Press, Mar. 31, 2017, p. 239.
Search report issued on Apr. 11, 2026 for counterpart Chinese patent application No. 202410486235.X, along with machine EN translation.

* cited by examiner

HUMAN MILK OLIGOSACCHARIDES FOR IMPROVING RESISTANCE OF ORGANISM AGAINST *STAPHYLOCOCCUS AUREUS* INFECTION

This application is the U.S. National Stage of International Application No. PCT/CN2021/085623, filed Apr. 6, 2021, which designates the U.S., published in Chinese, and claims priority under 35 U.S.C. § 119 or 365(c) to Chinese Application No. 202010259662.6, filed Apr. 3, 2020. The entire teachings of the above applications are incorporated herein by reference.

FIELD OF THE INVENTION

The present invention relates to the field of food and pharmaceutical products, in particular to human milk oligosaccharides and use thereof.

BACKGROUND

Over the last millennium, literature have documented higher rates of morbidity and mortality in non-breastfed infants as compared to breastfed infants. Human milk not only provides the necessary nutrition for infants, but the active ingredients in human milk also protect infants' intestinal development and immunity. Breastfed infants had higher abundances of beneficial bacteria, especially Bifidobacteria and Lactobacilli, in the gut microbiota compared with formula-fed infants.

The transmission of human milk through gut flora, together with active ingredients such as human milk oligosaccharides and cytokines in human milk, establishes a healthy intestinal flora for the newborn. Infants ingest 107 to 108 bacteria, including Lactobacilli and Bifidobacteria, through human milk each day. These bacteria are directly transmitted to the infants through human milk, and some of them can colonize the infant's gut, promoting the establishment of gut microbiota early in life. The establishment of an infant's gut microbiome has short-term and life-long effects on the gut, immune system and health.

Human milk oligosaccharides (HMOs) are the third most abundant substances in human milk in addition to lactose and fat. The total content of HMO varies through lactation and is approximately 20 to 24 g/L in colostrum, and 12 to 14 g/L in mature milk. Each human milk oligosaccharides has a core structure of lactose at the reducing end, while most have polylactosamine as the structural backbone and modified with fucose, sialic acid or both at the end of the chain. Human milk oligosaccharides are mainly composed of three categories: (1) fucosylated-oligosaccharides, represented by 2'-fucosyl-oligosaccharides and 3-fucosyl-oligosaccharides; (2) sialylated oligosaccharides, represented by 3'-sialyllactose and 6'-sialyllactose; (3) oligosaccharides formed with the core structure free of fucosyl or sialyl, represented by lacto-N-tetraose and lacto-N-neotetraose.

The composition and concentration of HMOs vary among individuals and are related to the Lewis-secretory status of nursing mothers. Since the raw material of infant formula powder is usually cow's milk, and cow's milk does not contain or contains little of these oligosaccharides, HMOs become a gap that infant formula must overcome to be closer to the composition of human milk.

In the 1990s, 2'-fucosyllactose (2'-FL), an common HMO found in human milk, was found to be effective in mitigating the toxicity of heat stable toxins in *Escherichia coli*; in 2003, this oligosaccharide was reported to inhibit the adherence and infection of *Campylobacter jejuni*. Subsequently, the three main functions of human milk oligosaccharides have been gradually reported and discovered: (1) inhibiting the adherence and infection of specific pathogens; (2) acting as prebiotics to promote the growth of bacteria in the intestinal symbiotic system; (3) directly slowing down the inflammatory response of mucous membranes to toxic stimuli. The first clinical intervention trial using 2'-FL demonstrated that the addition of this specific ingredient to a low-calorie formula was not only safe, but also allowed formula-fed infants to grow at rates comparable to breastfed infants. 2'-FL is also used as a nutritional supplement for adults to relieve irritable bowel syndrome or inflammatory bowel diseases, or as a prebiotic to maintain the balance of intestinal flora.

Intestinal flora is an important constituent of the human intestinal micro-ecosystem and plays an important role in human health, such as providing essential nutrients, producing vitamin K, assisting the digestive process and promoting angiogenesis and intestinal nerve actions. Prebiotics are regarded as a micro-ecosystem managing tool to improve the health of the body by altering, regulating and reorganizing the existing gut microbiota.

At present, in the field of infant formula, supplementary food, and nutritional supplements, there is a need for solutions to relieve the intestinal discomfort of infants and toddlers and improve their ability to resist infection by pathogenic bacteria (such as *Staphylococcus aureus*). At the same time, for children over 3 years old, adolescents and adults, there is also a need for solutions to relieve intestinal discomfort and improve their ability to resist infection by pathogenic bacteria (such as *Staphylococcus aureus*). *Caenorhabditis elegans* (*C. elegans*), a model organism, has good application prospects in pre-clinical research and evaluation. It has a short life cycle (21 days), is replicable and reproducible, easy to operate, is transparent, and easy to cultivate. Its genome has been fully sequenced, and a quarter of its genes are homologous to the human genome. Gene-mutated nematode organisms produced by editing the nematode's genes can be used as an experimental tool for genetic analysis. Nematodes are not currently regarded as an animal in European legislation. It is widely used as in vitro assays, e.g., in transcriptomics, proteomics, and metabolomics, etc. As a model organism, it is often used as the first step in the evaluation of raw materials. Before the design of functional raw materials, in vitro enzyme or cell experiments, mouse models and clinical experiments, nematodes are often used as a high-throughput means to screen tested raw materials for certain properties.

*Staphylococcus aureus* (*S. aureus*) is a gram-positive bacterium belonging to the genus *Staphylococcus* and is a common food-borne pathogenic microorganism. It exists widely in the natural environment, and under certain conditions, it can produce enterotoxins and can cause food poisoning, and was responsible for many foodborne microbial food poisoning accidents caused by *Staphylococcus aureus*. After the human body is infected by *Staphylococcus aureus*, common symptoms of food poisoning such as nausea, vomiting, and dizziness may occur, and symptoms of enteritis, pneumonia, skin infection, wound infection and ulceration, meningitis and the like may occur.

SUMMARY OF THE INVENTION

The present inventors have creatively discovered that some human milk oligosaccharides can enhance the resistance of organisms against *Staphylococcus aureus* infection, thus providing the following invention.

In one aspect, the present invention provides use of human milk oligosaccharide in the preparation of a nutritional composition or medicament, wherein the nutritional composition or medicament is used for preventing and/or treating a disease associated with *Staphylococcus aureus* infection in an individual, or for alleviating discomfort associated with *Staphylococcus aureus* infection, or for improving an individual's resistance against *Staphylococcus aureus* infection, or for improving an individual's innate immunity and/or anti-aging; the human milk oligosaccharide being selected from the group consisting of: 2'-fucosyllactose, 3-fucosyllactose, lacto-N-tetraose, 6'-sialyllactose and any combination thereof, and a combination formed by 3'-sialyllactose together with one or more selected from 2'-fucosyllactose, 3-fucosyllactose, lacto-N-tetraose, and 6'-sialyllactose.

In one aspect, the present invention provides a nutritional composition or medicament comprising a human milk oligosaccharide which is selected from the group consisting of: 2'-fucosyllactose, 3-fucosyllactose, lacto-N-tetraose, 6'-sialyllactose and any combination thereof, and a combination formed by 3'-sialyllactose together with one or more selected from 2'-fucosyllactose, 3-fucosyllactose, lacto-N-tetraose, and 6'-sialyllactose; when the nutritional composition or medicament is liquid, a content of the human milk oligosaccharides in the nutritional composition or medicament is 0.03 to 12 g/L, preferably 0.03 to 6 g/L; when the nutritional composition or medicament is solid (e.g., powder), a content of the human milk oligosaccharide in the nutritional composition or medicament is 0.02 to 9.09 g/100 g, preferably 0.02 to 4.55 g/100 g.

In some embodiments, where the nutritional composition or medicament is solid (e.g., powder), the nutritional composition or medicament may be dispersed or dissolved in a medium to obtain a liquid at a certain concentration in compliance with its conventional used dose (e.g., the dose recommended on the instructions or packaging of the nutritional composition or medicament). Exemplary media include, but are not limited to, water.

In some embodiments, the nutritional composition is a dairy powder, such as a formulated milk powder, and in some embodiments, it may be reconstitute according to the water/milk powder ratio recommended on the packaging of the nutritional composition. The content of human milk oligosaccharides (e.g., 2'-fucosyl lactose, 3-fucosyl lactose, lacto-N-tetraose, 6'-sialyllactose, or 3'-sialyllactose) in the formula milk obtained after reconstitution is close to the content of the human milk oligosaccharides in human milk.

In certain embodiments, the nutritional composition or medicament is liquid, and the content of the human milk oligosaccharides in the nutritional composition or medicament is 0.03 to 0.05 g/L, 0.05 to 0.1 g/L, 0.1 to 0.5 g/L, 0.5 to 1 g/L, 1 to 2 g/L, 2 to 3 g/L, 3 to 4 g/L, 4 to 5 g/L, 5 to 6 g/L, 6 to 7 g/L, 7 to 8 g/L, 8 to 9 g/L, 9 to 10 g/L, 10 to 11 g/L, or 11 to 12 g/L.

In certain embodiments, the nutritional composition or medicament is solid (e.g., powder), and the content of the human milk oligosaccharides in the nutritional composition or medicament is 0.02 to 0.05 g/100 g, 0.05 to 0.07 g/100 g, 0.07 to 0.1 g/100 g, 0.1 to 0.5 g/100 g, 0.5 to 1 g/100 g, 1 to 2 g/100 g, 2 to 3 g/100 g, 3 to 4 g/100 g, 4 to 5 g/100 g, 5 to 6 g/100 g, 6 to 7 g/100 g, 7 to 8 g/100 g, 8 to 9 g/100 g or 9 to 9.09 g/100 g.

In certain embodiments, the nutritional composition or medicament is used for preventing and/or treating a disease associated with *Staphylococcus aureus* infection in an individual, or alleviating discomfort associated with *Staphylococcus aureus* infection in an individual, or improving the individual's resistance against *Staphylococcus aureus* infection, or improving the individual's innate immunity and/or anti-aging.

In one aspect, the present invention provides a method for preventing and/or treating a disease associated with *Staphylococcus aureus* infection in an individual, or alleviating discomfort associated with *Staphylococcus aureus* infection in an individual, or improving the individual's resistance against *Staphylococcus aureus* infection, or improving the individual's innate immunity and/or anti-aging, and the human milk oligosaccharide is selected from the group consisting of: 2'-fucosyllactose, 3-fucosyllactose, lacto-N-tetraose, 6'-sialyllactose and any combination thereof, and a combination formed by 3'-sialyllactose together with one or more selected from 2'-fucosyllactose, 3-fucosyllactose, lacto-N-tetraose, and 6'-sialyllactose.

In the present invention, 2'-fucosyllactose (2'-FL or 2-FL) is a trisaccharide structure formed by fucose and lactose, which is a representative substance of fucosylated oligosaccharides. This commercially available material is usually prepared by microbial fermentation and has the same structure as 2'-fucosyllactose found in human milk.

3-fucosyllactose (3-FL), a trisaccharide structure formed by fucose and lactose, is an isomer of 2'-fucosyllactose and a representative substance of fucosylated oligosaccharides. This substance can be prepared by microbial fermentation and has the same structure as 3-fucosyllactose found in human milk.

Lacto-N-tetraose (LNT), a hexasaccharide structure formed by lactose and tetraose, is a representative substance of oligosaccharides of which core sugar chain is the basic structure and does not contain a fucosyl group or a sialyl group. This substance can be prepared by microbial fermentation and has the same structure as lacto-N-tetraose found in human milk.

3'-sialyllactose (3'-sialyllactose, 3'-SL), a trisaccharide structure formed by sialic acid and lactose, is an isomer of 6'-sialyllactose and a representative substance of sialylated oligosaccharides. This substance is prepared by microbial fermentation and has the same structure as 3'-sialyllactose found in human milk.

6'-sialyllactose (6'-SL), a trisaccharide structure formed by sialic acid and lactose, is an isomer of 3'-sialyllactose and a representative substance of sialylated oligosaccharides. This substance is prepared by microbial fermentation and has the same structure as 6'-sialyllactose found in human milk.

In the use, or the approach of prevention and/or treatment of a disease, or the method of alleviating discomfort or improving resistance provided by the present invention, the human milk oligosaccharide may be administered at a dose of 0.012 to 12 g/day.

In certain embodiments, the human milk oligosaccharides is administered at a dose of 0.012 to 0.03 g/day, 0.03 to 0.04 g/day, 0.04 to 0.1 g/day, 0.1 to 0.2 g/day, 0.2 to 0.225 g/day, 0.225 to 0.3 g/day, 0.3 to 1 g/day, 1 to 2 g/day, 2 to 2.4 g/day, 2.4 to 3 g/day, 3 to 4 g/day, 4 to 4.5 g/day, 4.5 to 4.8 g/day, 4.8 to 5 g/day, 5 to 6 g/day, 6 to 9 g/day or 9 to 12 g/day. In certain embodiments, the applicable population for the dosage is human (e.g., infants or toddlers, e.g., infants of 0 to 6 months).

Optionally, the human milk oligosaccharide is present in formula milk powder. Formula milk can be obtained by reconstitute formula milk powder according to the water/ milk powder ratio recommended on the formula milk powder package, and a certain amount of formula milk is administered to an individual with reference to the milk intake (for example, 400 to 1000 mL/day, such as 400 to 750 mL/day or 750 to 1000 mL/day) of the individual (such as an infant of 0 to 6 months).

In one aspect, the present invention provides a method for reducing infectivity of *Staphylococcus aureus*, and the method comprises contacting *Staphylococcus aureus* with an effective amount of a human milk oligosaccharide selected from the group consisting of: 2'-fucosyllactose, 3-fucosyllactose, lacto-N-tetraose, 6'-sialyllactose and any combination thereof, and a combination formed by 3'-sialyllactose together with one or more selected from 2'-fucosyllactose, 3-fucosyllactose, lacto-N-tetraose, and 6'-sialyllactose.

In certain embodiments, the contacting is performed in vivo to reduce the infectivity of *Staphylococcus aureus* in an individual. In certain embodiments, the contacting comprises administering a human milk oligosaccharide to an individual in need thereof. In certain embodiments, the individual has or is suspected of having, or is at risk for, a disease associated with *Staphylococcus aureus* infection. In certain embodiments, the *Staphylococcus aureus* is located in the gut, lung, skin, blood, ear, nose, umbilical cord, and/or brain of the individual.

In certain embodiments, the contacting is performed in vitro (e.g., a cell line or a cell from an individual) to reduce the infectivity of *Staphylococcus aureus* in the cells in vitro.

In certain embodiments, the effective amount is 0.012 to 12 g/day, such as 0.012 to 0.03 g/day, 0.03 to 0.04 g/day, 0.04 to 0.1 g/day, 0.1 to 0.2 g/day, 0.2 to 0.225 g/day, 0.225 to 0.3 g/day, 0.3 to 1 g/day, 1 to 2 g/day, 2 to 2.4 g/day, 2.4 to 3 g/day, 3 to 4 g/day, 4 to 4.5 g/day, 4.5 to 4.8 g/day, 4.8 to 5 g/day, 5 to 6 g/day, 6 to 9 g/day or 9 to 12 g/day. In certain embodiments, the applicable population for the effective amount is human (e.g., infants or toddlers, e.g., infants of 0 to 6 months).

Optionally, the human milk oligosaccharide is present in formula milk powder. Formula milk can be obtained by reconstitution of formula milk powder according to the water/milk powder ratio recommended on the formula milk powder package, and a certain amount of formula milk is administered to an individual with reference to the milk intake (such as 400 to 1000 mL/day, such as 400 to 750 mL/day or 750 to 1000 mL/day) of the individual (such as an infant of 0 to 6 months).

In some embodiments, the effective amount is at least 1.5 mg/mL (e.g., 1.5 mg/mL to 10 mg/mL, 10 mg/mL to 30 mg/mL, or at least 30 mg/mL). In some embodiments, the applicable population for the effective amount is a nematode (e.g., *Caenorhabditis elegans*).

In some embodiments, the method is not used for the purpose of preventing, treating or diagnosing a disease (e.g., for scientific research).

In the present invention, a "nutritional composition" refers to a nutritional preparation and a nutritional product, such as a nutritional supplement, functional food, a beverage product, a diet replacement or a food additive. Such nutritional compositions may be nutritionally complete and may include, for example, vitamins, minerals, carbohydrates, proteins, fats, etc., and thus may be used as a sole source of nutrition providing essentially all daily essential amounts of vitamins, minerals, carbohydrates, fats, proteins, etc. Thus, human milk oligosaccharides may be provided, e.g., in the form of nutritional compositions suitable for oral or gavage feeding, such as complete formula diet. In addition, human milk oligosaccharides can be provided as part of the diet, i.e. nutritional supplements. In the present invention, when the nutritional composition is a food, it may not be used for preventing and/or treating diseases.

In certain embodiments, the nutritional composition contemplated by the present invention is a formula, such as an infant formula (e.g., infant formula, follow-up formula, toddler formula, infant formula for special medical use).

In the present invention, "formula food" refers to nutritional compositions designed for infants, toddlers, children, adults, or a combination thereof, containing sufficient nutrients (such as proteins, carbohydrates, lipids, vitamins, minerals and electrolytes) that may serve as supplemental, primary or sole nutritional sources.

In the present invention, "infant" refers to a person up to about 12 months of age, including infants from 0 to about 4 months old, infants from about 4 to about 8 months old, and infants from about 8 to about 12 months old; "older infant" refers to a person from about 6 to about 12 months of age; "toddler" refers to a person over 12 months of age and up to 3 years old; "child" refers to a person over the age of 3 and under the age of 12.

In the present invention, "infant formula" refers to a replacement or substitute for human milk that is suitable for infants and the energy and nutrient contents thereof can meet the general nutritional needs of infants from 0 to 6 months of age.

In the present invention, "follow-up formula" refers to a formula suitable for infants 7-12 months of age, and the nutritional composition thereof can meet part of the nutritional needs of normal older infants and can be used as a replacement or substitute for human milk.

In the present invention, "toddler formula" refers to a formula suitable for toddlers aged 13-36 months, and the nutritional composition thereof can meet part of the nutritional needs of normal toddlers and can be used as a replacement or substitute for human milk.

In the present invention, "infant formula for special medical use" refers to a formula designed to meet the nutritional needs of infants with special medical conditions such as special disorders, diseases or medical conditions; when taken alone or in combination with other foods under the guidance of a physician or clinical dietitian, its energy and nutrients can meet the growth and development needs of infants with special medical conditions from 0 months to 6 months of age.

In certain embodiments, in addition to human milk oligosaccharides, the infant formula (e.g., infant formula, follow-up formula, toddler formula, or infant formula for special medical use) may include the following ingredients or any combination thereof: protein as an energy source (e.g., milk protein, soy protein, alpha-lactalbumin, beta-casein), fats (e.g., linoleic acid, α-linolenic acid, 1,3-dioleo-2-palmitic acid triglyceride) and carbohydrates (e.g., lactose, polymers of lactose and glucose), vitamins (e.g., vitamin A, vitamin D, vitamin K, vitamin B1, vitamin B2, vitamin B6, vitamin B12, niacin, folic acid, vitamin C, biotin, choline), minerals (e.g., sodium, potassium, copper, magnesium, iron, zinc, manganese, calcium, phosphorus, iodine, chlorine, selenium); optionally, the infant formula may further comprise dietary fibers, nucleotides, inositol, taurine, L-carnitine, docosahexaenoic acid, eicosatetraenoic acid, or any combination thereof.

In certain embodiments, the nutritional compositions (e.g., formula) of the present invention are liquid or powdered products produced and processed only by physical methods.

In certain embodiments, the nutritional composition according to the present invention is a supplementary food for infants and toddlers.

In certain embodiments, the nutritional composition according to the present invention is a dairy product (e.g., 1st stage formula milk powder, 2nd stage formula milk powder, 3rd stage formula milk powder, fermented milk).

In certain embodiments, the nutritional composition according to the present invention is a nutritional supplement. The nutritional supplement can be in the form of pills, capsules, tablets, granules, liquid or other forms suitable for oral or gavage feeding. In certain embodiments, the nutritional supplement further contains one or more carriers or excipients. Suitable carriers or excipients may be selected from the group consisting of: sugars (e.g., lactose, sucrose, mannitol or sorbitol), cellulosic products (e.g., corn starch, wheat starch, rice starch, potato starch, gelatin, tragacanth, methyl cellulose, hydroxypropylmethylcellulose, sodium carboxymethylcellulose and/or polyvinylpyrrolidone), cross-linked polyvinylpyrrolidone, agar, alginic acid or a salt thereof (e.g., sodium alginate), and water.

In certain embodiments, in the nutritional composition or medicament according to the present invention, the human milk oligosaccharide is a single active ingredient that can prevent and/or treat a disease associated with *Staphylococcus aureus* infection in an individual, or alleviate discomfort associated with *Staphylococcus aureus* infection, or improve an individual's resistance against *Staphylococcus aureus* infection, or improve an individual's innate immunity and/or anti-aging. In certain embodiments, the nutritional composition or medicament also contains other active ingredients useful in the prevention and/or treatment of a disease associated with *Staphylococcus aureus* infection in an individual, or alleviation of discomfort associated with *Staphylococcus aureus* infection, or improvement of an individual's resistance against *Staphylococcus aureus* infection, or improvement of an individual's innate immunity and/or anti-aging.

In certain embodiments, the medicaments of the present invention may be in solid, semi-solid, gel or liquid form preparations such as tablets, capsules, powders, granules, solutions, depositories, gels and injections. Formulations suitable for oral administration may be presented as discrete units such as capsules, tablets, lozenges. Other formulations include: suspensions in aqueous or non-aqueous liquids such as syrups, elixirs, gels or emulsions. In certain embodiments, the medicament further contains one or more pharmaceutically acceptable carriers or excipients. Suitable carriers or excipients may be selected from the group consisting of: sugars (e.g., lactose, sucrose, mannitol or sorbitol), cellulosic products (e.g., corn starch, wheat starch, rice starch, potato starch, gelatin, tragacanth, methyl cellulose, hydroxypropylmethylcellulose, sodium carboxymethylcellulose and/or polyvinylpyrrolidone), cross-linked polyvinylpyrrolidone, agar, alginic acid or a salt thereof (e.g., sodium alginate), and water.

In certain embodiments, the human milk oligosaccharides, nutritional compositions or medicaments contemplated by the present invention may be administered to an individual via the enteral route, e.g., orally administered in the form of powders, powdered beverages, liquids, capsules or pills. In certain embodiments, the human milk oligosaccharide is administered to the individual in a single dose, while in other embodiments, multiple doses are administered over a specified period of time. For example, in certain embodiments, the human milk oligosaccharide is administered 1-5 times, 5-10 times, or more than 10 times per day. In certain embodiments, the administration lasts for about 1 week, about 2 weeks, about 3 weeks, about 4 weeks, about 1 month, about 5 weeks, about 6 weeks, about 2 months, about 3 months, about 4 months, about 5 months, about 6 months, or about a year. In certain embodiments, administration lasts until the individual's clinical symptoms improved. In the present invention, any combination of 2'-fucosyllactose, 3-fucosyllactose, lacto-N-tetraose, and 6'-sialyllactose can be selected from the following combinations:

(1) a combination consisting of 2'-fucosyllactose and 3-fucosyllactose;

(2) a combination consisting of 2'-fucosyllactose and lacto-N-tetraose;

(3) a combination consisting of 2'-fucosyllactose and 6'-sialyllactose;

(4) a combination consisting of 2'-fucosyllactose, 3-fucosyllactose and lacto-N-tetraose;

(5) a combination consisting of 2'-fucosyllactose, 3-fucosyllactose and 6'-sialyllactose;

(6) a combination consisting of 2'-fucosyllactose, lacto-N-tetraose and 6'-sialyllactose;

(7) a combination consisting of 3-fucosyllactose and lacto-N-tetraose;

(8) a combination consisting of 3-fucosyllactose and 6'-sialyllactose;

(9) a combination consisting of 3-fucosyllactose, lacto-N-tetraose and 6'-sialyllactose;

(10) a combination consisting of lacto-N-tetraose and 6'-sialyllactose; and

(11) a combination consisting of 2'-fucosyllactose, 3-fucosyllactose, lacto-N-tetraose and 6'-sialyllactose.

In the present invention, a combination formed by 3'-sialyllactose together with one or more of 2'-fucosyllactose, 3-fucosyllactose, lacto-N-tetraose and 6'-sialyllactose may be selected from the combination form by 3'-sialyllactose with any of the above (1)-(11).

In certain embodiments, the human milk oligosaccharide is a combination composed of at least four of 2'-fucosyllactose (2'-FL), 3-fucosyllactose (3-FL), lacto-N-tetraose (LNT), 3'-sialyllactose (3'-SL), and 6'-sialyllactose (6'-SL), with a ratio of the human milk oligosaccharides of 2'-FL: 3-FL:LNT: 3'-SL: 6'-SL=(1%-60%):(0-50%):(5%-40%):(2%-85%):(0-12%), preferably (2%-55%):(0-44%):(10%-35%):(5%-80%):(0-10%), more preferably (2%-53%):(0-41%):(10%-32%):(5%-80%):(0-8%), and further preferably (5%-53%):(21%-41%):(16%-32%):(5%-22%):(0-5%). In these embodiments, the content of 3'-SL in the composition is preferably greater than 5%.

In certain embodiments, the human milk oligosaccharide is a combination composed of 2'-fucosyl lactose (2'-FL), 3-fucosyl lactose (3-FL), lacto-N-tetraose (LNT) and 3'-sialyllactose (3'-SL), with a ratio of the human milk oligosaccharides of 2'-FL: 3-FL:LNT: 3'-SL=(1%-60%):(1%-50%):(5%-40%):(2%-90%), preferably (1%-56%):(1%-45%):(10%-35%):(5%-88%), more preferably (2%-56%):(1%-41%):(11%-32%):(5%-86%), and further preferably (5%-56%):(22%-41%):(17%-32%):(5%-22%). In these embodiments, the content of 3'-SL in the composition is preferably greater than 5%.

In certain embodiments, the human milk oligosaccharide is a combination composed of 2'-fucosyllactose (2'-FL), lacto-N-tetraose (LNT), 3'-sialyllactose (3'-SL) and 6'-sialyllactose (6'-SL), with a ratio of the human milk oligosaccharides of 2'-FL:LNT: 3'-SL: 6'-SL=(1%-75%):(5%-65%):(1%-85%):(1%-15%), preferably (2%-70%):(10%-60%):(2%-80%):(1%40%), more preferably (2%-

67%):(10%-54%):(6%-80%):(1%-8%), more preferably (9%-67%):(20%-54%):(6%-37%):(1%-6%). In these embodiments, the content of 3'-SL in the composition is preferably greater than 5%.

In certain embodiments, the human milk oligosaccharide is a combination composed of 2'-fucosyllactose (2'-FL), 3-fucosyllactose (3-FL), lacto-N-tetraose (LNT), 3'-sialyllactose (3'-SL) and 6'-sialyllactose (6'-SL), with a ratio of the five human milk oligosaccharides of 2'-FL: 3-FL:LNT: 3'-SL: 6'-SL=(5%-53%):(21%-44%):(16%-32%):(5%-22%):(0-5%), where the content of 6'-SL is greater than 0.

In certain embodiments, the ratio of the five human milk oligosaccharides is 2'-FL: 3-FL:LNT: 3'-SL: 6'-SL=(5%-10%, 10%-20%, 20%-30%, 30%-40%, 40%-50%, or 50%-53%):(21%-25%, 25%-30%, 30%-35%, 35%-40%, or 40%-44%):(16%-20%, 20%-24%, 24%-30%, or 30%-32%):(5%-8%, 8%-12%, 12%-16%, 16%-18%, or 18%-22%):(0-1%, 1%-2%, 2%-3%, 3%-4%, or 4%-5%).

In certain embodiments, the ratio of the five human milk oligosaccharides is 2'-FL: 3-FL:LNT: 3'-SL: 6'-SL=(50%-53%):(21%-25%):(16%-20%):(5%-8%):(4%-5%).

In certain embodiments, the ratio of the five human milk oligosaccharides is 2'-FL: 3-FL:LNT: 3'-SL: 6'-SL=53%: 21%: 16%: 5%: 5%.

In the present invention, when the human milk oligosaccharides are present in the separate form of 2'-fucosyllactose, 3-fucosyllactose, lacto-N-tetraose or 6'-sialyllactose, the content or dose of the human milk oligosaccharides refers to the content or dose of separate oligosaccharides. When the human milk oligosaccharides are present in a combination, the content or dose of human milk oligosaccharides refers to the content or dose of the combination.

In the present invention, the disease or discomfort associated with *Staphylococcus aureus* infection includes, but is not limited to:

(1) food poisoning caused by *Staphylococcus aureus*, including nausea, vomiting, dizziness, etc.;

(2) illness such as enteritis and pneumonia caused by *Staphylococcus aureus* infection;

(3) skin infection, wound ulcer, etc. caused by *Staphylococcus aureus* infections;

(4) meningitis and the like caused by *Staphylococcus aureus* infection.

For the purposes of the present invention, an "individual" may be human or a non-human animal. Exemplary human individuals include human individuals (referred to as patients) suffering from a disease or discomfort (such as those described herein) or normal individuals. "Non-human animal" includes all vertebrates and non-vertebrates, such as non-mammals (e.g., birds, amphibians, reptiles) and mammals, such as non-human primates, domestic and/or domesticated animals (e.g., sheep, dogs, cats, cows, pigs, etc.). In the present invention, an "individual" may also be a nematode, such as *Caenorhabditis elegans*.

In certain embodiments, the individual is an infant, toddler, child, or adult (e.g., an adult over the age of 60).

In the present invention, "anti-aging" includes delaying aging and even death caused by *Staphylococcus aureus* infection, that is, "anti-aging" includes prolonging lifespan.

Beneficial Effects

The inventors found that 2'-fucosyllactose, 3-fucosyllactose, lacto-N-tetraose, 6'-sialyllactose can increase the survival rate of nematodes infected by *Staphylococcus aureus*, demonstrating that these human milk oligosaccharides can be used to improve the body's ability to cope with or resistance against *Staphylococcus aureus* infection, or to enhance individual innate immunity and/or anti-aging. In particular, 6'-sialyllactose and 3-fucosyllactose have a prominent protective effect and have the potential to function at lower concentrations. Furthermore, combinations of these human milk oligosaccharides (e.g., a combination of 3'-sialyllactose together with 2'-fucosyllactose, 3-fucosyllactose, lacto-N-tetraose, 6'-sialyllactose) also show a certain synergistic effect.

These human milk oligosaccharides can be used to prevent or treat a disease associated with *Staphylococcus aureus* infection, or to relieve discomfort associated with *Staphylococcus aureus* infections such as food poisoning, enteritis, pneumonia, skin infection or wound ulcers, meningitis etc., or used to enhance individual innate immunity and/or anti-aging, can be added to infant food (including infant formula, supplementary foods, nutritional supplements), and nutritional supplements or food for children or adults to enhance the individual's resistance to *Staphylococcus aureus* infection, or enhance the individual's innate immunity and/or anti-aging, which have a broad application prospect.

DETAILED DESCRIPTION OF THE INVENTION

Figure 1:
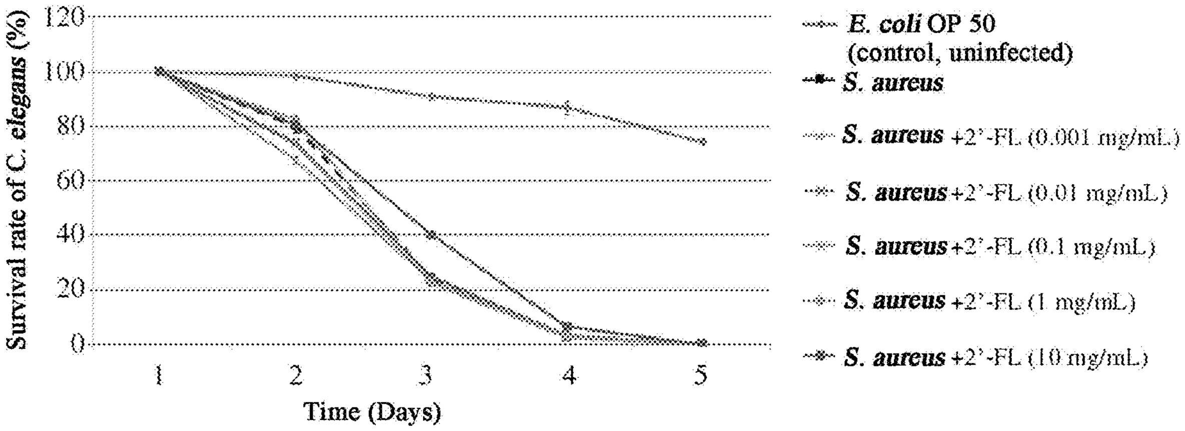
FIG. 1 shows the effect of different doses of the human milk oligosaccharide 2'-FL on the survival rate of *C. elegans* when infected by *Staphylococcus aureus*. The interventions (HMOs) added during the infection phase were the same for each group in the figure as for the culture phase, respectively.

The technical solutions in the embodiments of the present invention will be clearly and fully described below in conjunction with the accompanying drawings in the embodiments of the present invention. Obviously, the described embodiments are only a part of, but not all of the embodiments of the present invention. Based on the embodiments of the present invention, all other embodiments obtainable by those of ordinary skill in the art fall within the scope of protection of the present invention.

Unless otherwise specifically defined, all technical and scientific terms used herein have the same meaning as commonly understood by those of ordinary skill in the relevant field.

In addition, to avoid repetition, the common procedures that are necessary for the experiments in each example, such as culture of strains, are listed below.

Materials and Methods

TABLE 1

Tested uman milk oligosaccharide samples

| Chinese Name | English Name | English Abbreviations |
|---|---|---|
| 2'- -岩藻糖基乳糖 | 2'-fucosyllactose | 2'-FL |
| 3- 岩藻糖基乳糖 | 3-fucosyllactose | 3-FL |
| 乳糖-N-四糖 | Lacto-N-Tetraose | LNT |
| 3'- -唾液酸基乳糖 | 3'-sialyllactose | 3'-SL |
| 6'- 唾液酸基乳糖 | 6'-sialyllactose | 6'-SL |
| 五种母乳低聚糖组合物 | Human Milk Oligosaccharide mix | HMO mix |

TABLE 2

Formulation of the tested human milk oligosaccharide compositions

| Ratios (%) | 2'-FL | 3-FL | LNT | 3'-SL | 6'-SL |
|---|---|---|---|---|---|
| Composition A | 53 | 21 | 16 | 5 | 5 |
| Composition G | 5 | 41 | 32 | 22 | 0 |
| Composition H | 30 | 30 | 25 | 12 | 3 |
| Composition J | 2 | 0 | 10 | 80 | 8 |

Human milk oligosaccharide solutions were prepared with distilled water and incubated in Petri dishes containing a nematode growth medium at different final concentrations (1, 10, and 30 mg/mL, respectively). To better determine the range of the ideal concentration, a preliminary screening on the dose-effect relationship of 2'-FL was first performed, and the 2'-FL concentrations used were 0.001, 0.01, 0.1, 1 and 10 mg/mL. For the HMO compositions, included were a test concentration of 8 mg/mL and a 15 mg/mL, respectively, after the addition into the nematode growth medium.

*Bifidobacterium animalis* BB-12 was grown in an MRS medium supplemented with 1% cysteine and incubated overnight at 37° C. in an anaerobic environment. Cells were harvested and rinsed with a saline solution, adjusted for bacterial concentration, and cultivited in plates containing nematode growth medium at a final concentration of $1\times10^8$CFU.

Nematode Infection Model and Lifespan Assay

Age-consistent nematodes were obtained and cultured in Petri dishes containing nematode agar media (nematode media containing *E. coli* OP50 as food) with different doses of HMO (1, 8, 10, 15, 30 mg/mL) for co-culture. After the nematodes came into adulthood, they were transferred to petri dishes inoculated with *Staphylococcus aureus* ATCC25923 (supplemented at approximately $10^8$ to $10^9$CFU/mL) to simulate the condition of infection by *Staphylococcus aureus*. The intervening substances (HMO) added in the infection stage of each group were the same as those in the culture stage. Two controls were used, one without the pathogen (*C. elegans* dish containing *E. coli* OP50) and one with *Staphylococcus aureus* infection without any intervention (dish with *Staphylococcus aureus* only). In addition, a group in which an intervening substance was added in the culture phase and no intervention in the infection phase, and a group in which the intervention substance was not added in the cultivation phase but added in the infection phase were set up.

Several days into the culture of the nematodes, their survival rate was counted on a daily basis. If the nematodes do not respond to the platinum wire, they were considered dead. Two independent assays were carried out for each condition (that is, unless otherwise specified, the experimental data in the examples were the results of two independent experiments).

Statistical comparative analysis of survival curves was performed, and log rank survival significance analysis was performed using the GraphPad Prism 4 or GraphPad Prism 9 statistical software package. One-way ANOVA was used to analyze for significant differences in survival rates among the groups on the third or fifth day of infection. For the comparison of the groups, an asterisk*represents the degree of the significant difference, with **indicating P<0.0001, and *indicating P<0.001. NS means not significant.

EXPERIMENTAL RESULTS

Figure 2:
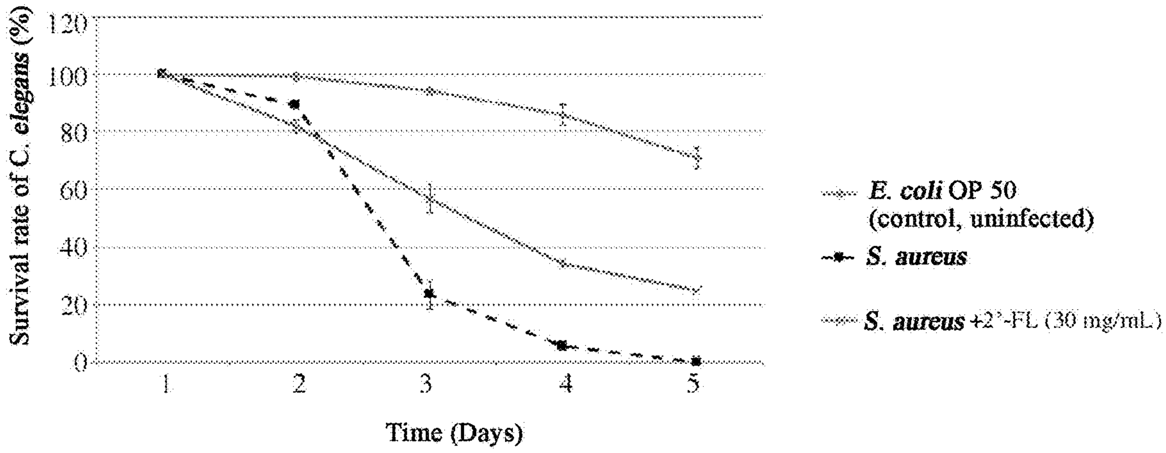
FIG. 2 shows the effect of a certain dose of the human milk oligosaccharide 2'-FL on the survival rate of *C. elegans* when infected by *Staphylococcus aureus*. The interventions (HMOs) added during the infection phase were the same for each group in the figure as for the culture phase, respectively.
Figure 3:
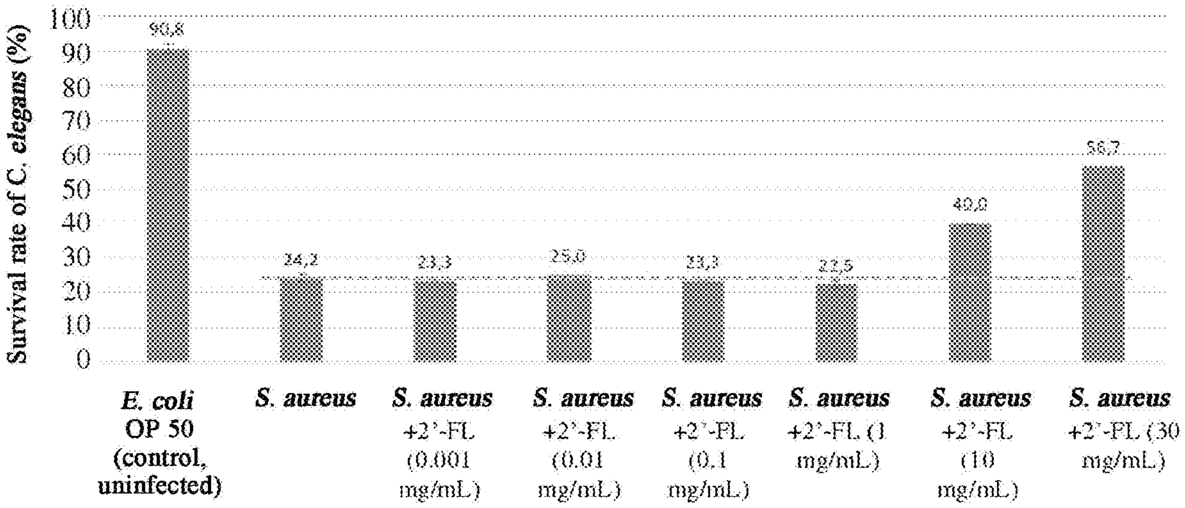
FIG. 3 shows the effect of multiple different doses of the human milk oligosaccharide 2'-FL on the survival rate of *C. elegans* on the third day of infection by *Staphylococcus aureus.*

Example 1. Effects of Different Concentrations of the Human Milk Oligosaccharide 2'-FL on the Survival Rate of Nematodes after *Staphylococcus aureus* Infection First, to determine the dose range of the HMO tested in the experiments, six different doses of 2'-FL were tested. As shown in FIG. 1, doses at 1 mg/mL or less did not show any effects, and 10 mg/mL caused a considerable increase in nematode survival rate which was significant (P<0.0001). Therefore, as shown in FIG. 2, higher doses were tested, and when the dose of 2'-FL reached 30 mg/mL, the protective effect was significantly increased, and the effect was significant (P<0.0001). Seen as such, 2'-FL had a significant protective effect against *Staphylococcus aureus*, which was dose-dependent and optimal at 30 mg/mL. The histogram in FIG. 3 shows the different effects of different doses of 2'-FL on the survival rate of nematodes after being infected by *Staphylococcus aureus* for 3 days, showing that the protective effect is more pronounced at higher concentrations.

Figure 4:
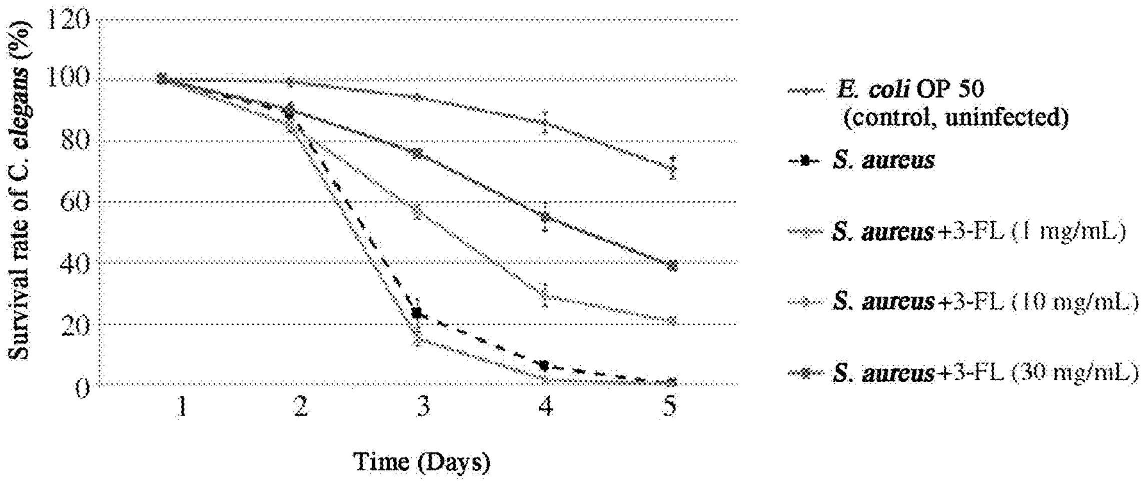
FIG. 4: pathogenic bacteria survival test using *Staphylococcus aureus* in the nematode model with 2'-FL tested at a concentration of 15 mg/mL. The interventions (HMOs) added during the infection phase were the same for each group in the figure as for the culture phase, respectively.

In another batch of experiments of the present invention, the improvement of the sole HMO 2'-FL at a concentration of 15 mg/mL on nematode survival rate after *Staphylococcus aureus* infection was also evaluated, as in the results shown in FIG. 4. It can be seen that at this concentration, 2'-FL alone significantly improves the survival rate of nematodes and significantly prolongs the lifespan of nematodes, demonstrating the regulation and enhancement of 2'-FL on the immune function of biological organisms, especially the innate immunity, and also showing a great potential of 2'-FL in improving the anti-aging of biological organisms.

Figure 5:
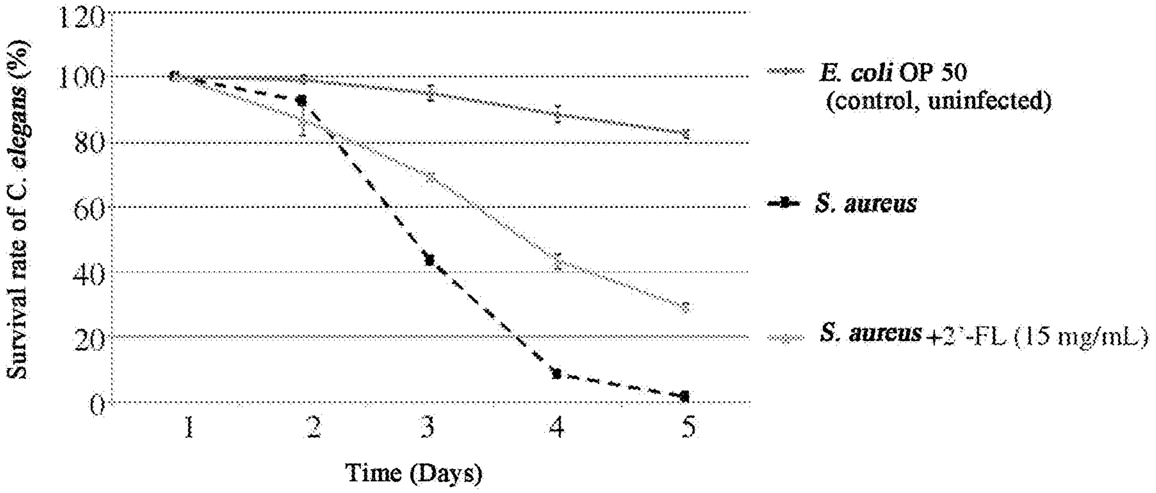
FIG. 5 shows the effect of different doses of the human milk oligosaccharide 3-FL on the survival rate of *C. elegans* when infected by *Staphylococcus aureus*. The interventions (HMOs) added during the infection phase were the same for each group in the figure as for the culture phase, respectively.
Figure 6:
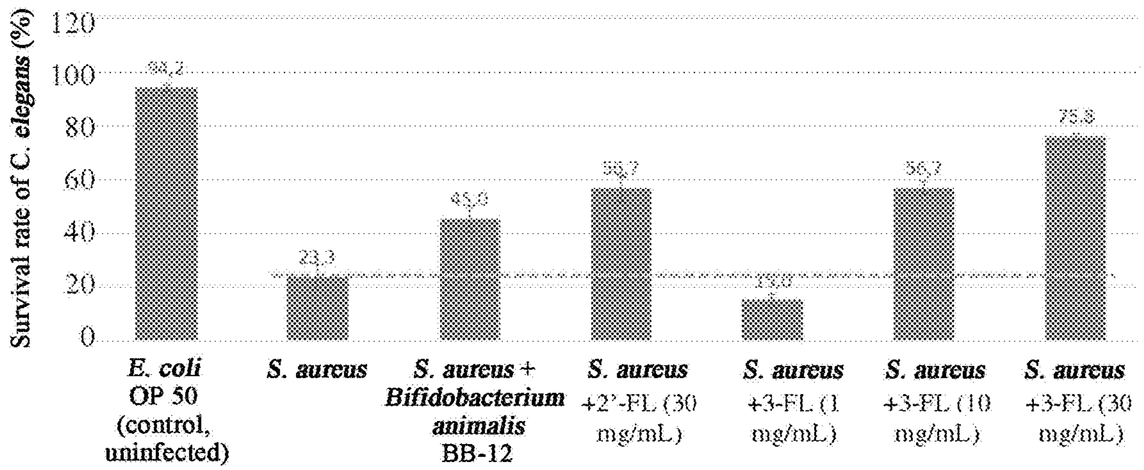
FIG. 6 shows a comparison of the different effects of different doses of the human milk oligosaccharides 2'-FL and 3-FL on the survival rate of *C. elegans* on the third day of infection by *Staphylococcus aureus.*

Example 2. Effect of Different Concentrations of the Human Milk Oligosaccharide 3-FL on Nematode Survival Rate after *Staphylococcus aureus* Infection As shown in FIG. 5, a dose-effect relationship was also observed for 3-FL, with greater protection shown at higher doses. At the concentration of 10 and 30 mg/mL, 3-FL had a better protective function (P<0.0001), with the effect maximized at 30 mg/mL. There was no effect at 1 mg/mL. As shown in FIG. 6, comparison of the data on the effect of 3-FL and 2'-FL as well as *Bifidobacterium animalis* BB-12 on the survival rate of nematodes showed that upon infection by *Staphylococcus aureus* for 3 days, the same effect was achieved with 3-FL at 10 mg/mL as that with 2'-FL at 30 mg/mL. As such, 3-FL was more effective in protecting nematodes from *Staphylococcus aureus* infection than 2'-FL at the same dose. It was deducted that 3-FL at less than 10 mg/mL had the potential to have a notably better protection on nematode survival in the presence of *Staphylococcus aureus* infection than that of the negative control group.

Figure 7:
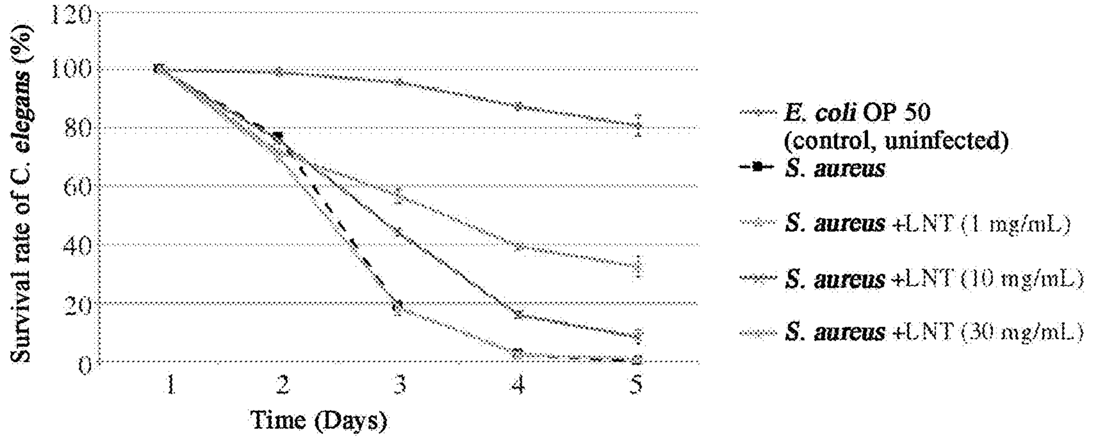
FIG. 7 shows the effect of different doses of the human milk oligosaccharide LNT on the survival rate of *C. elegans* when infected by *Staphylococcus aureus*. The interventions (HMOs) added during the infection phase were the same for each group in the figure as for the culture phase, respectively.
Figure 8:
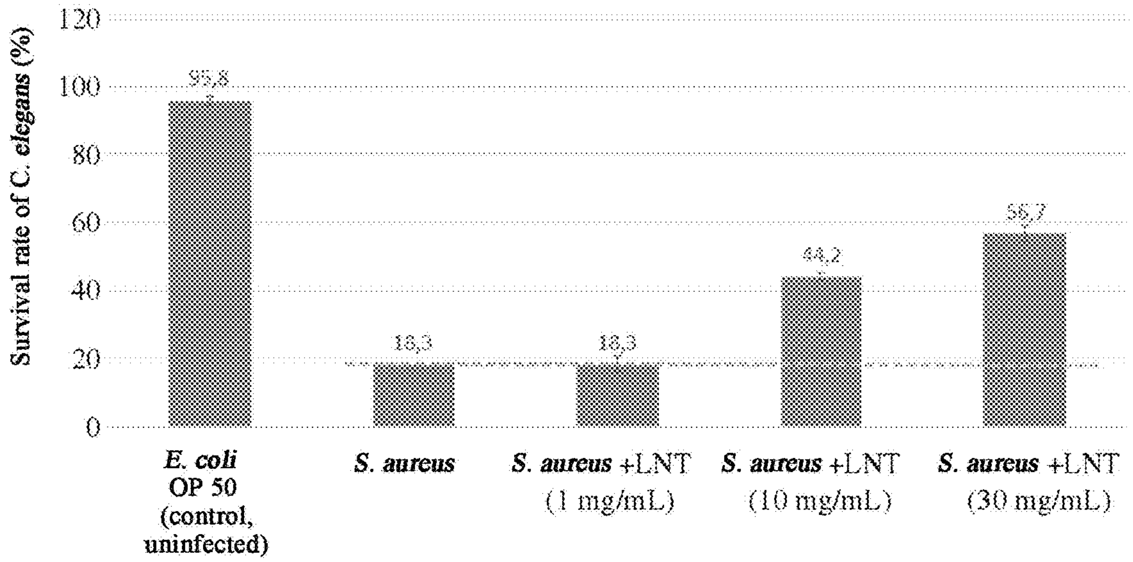
FIG. 8 shows the effect of several different doses of the human milk oligosaccharide LNT on the survival rate of *C. elegans* on the third day of infection by *Staphylococcus aureus.*

Example 3. Effects of Different Concentrations of the Human Milk Oligosaccharide LNT on Nematode Survival Rate after *Staphylococcus aureus* Infection As shown in FIG. 7, similarly, when LNT was added at a concentration of 1 mg/mL, the survival rate of *Caenorhabditis elegans* (in short, nematodes) after *Staphylococcus aureus* infection was not greatly improved, but when LNT was added at a concentration of 10 mg/mL mL or 30 mg/mL, the survival rate of nematodes after *Staphylococcus aureus* infection was significantly improved. Seen as such, LNT also has a dose-effect relationship in the regulation of nematode growth after *Staphylococcus aureus* infection. The histogram in FIG. 8 shows the different effects of different doses of LNT on the survival rate of nematodes after being infected by *Staphylococcus aureus* for 3 days, showing that the protective effect is more pronounced at higher concentrations.

Figure 9:
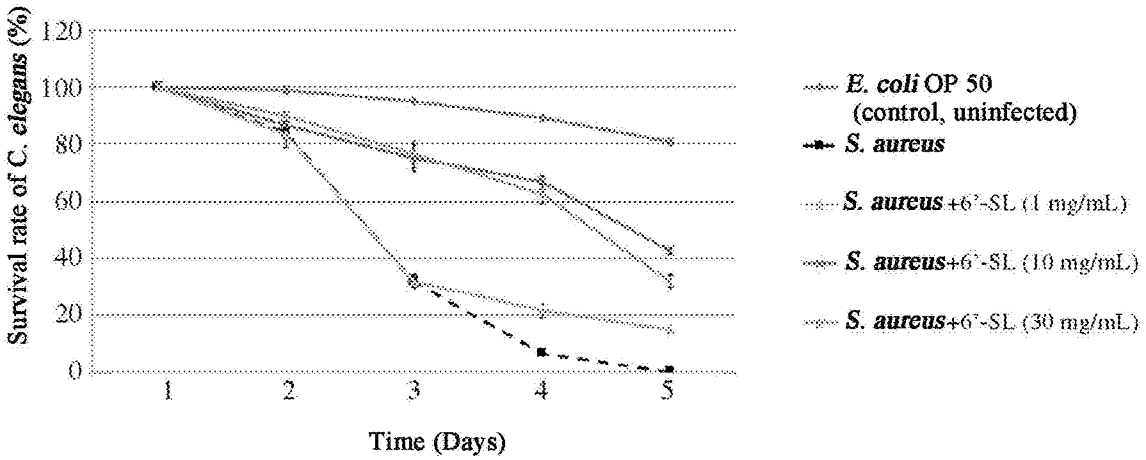
FIG. 9 shows the effect of different doses of the human milk oligosaccharide 6'-SL on the survival rate of *C. elegans* when infected by *Staphylococcus aureus*. The interventions (HMOs) added during the infection phase were the same for each group in the figure as for the culture phase, respectively.
Figure 10:
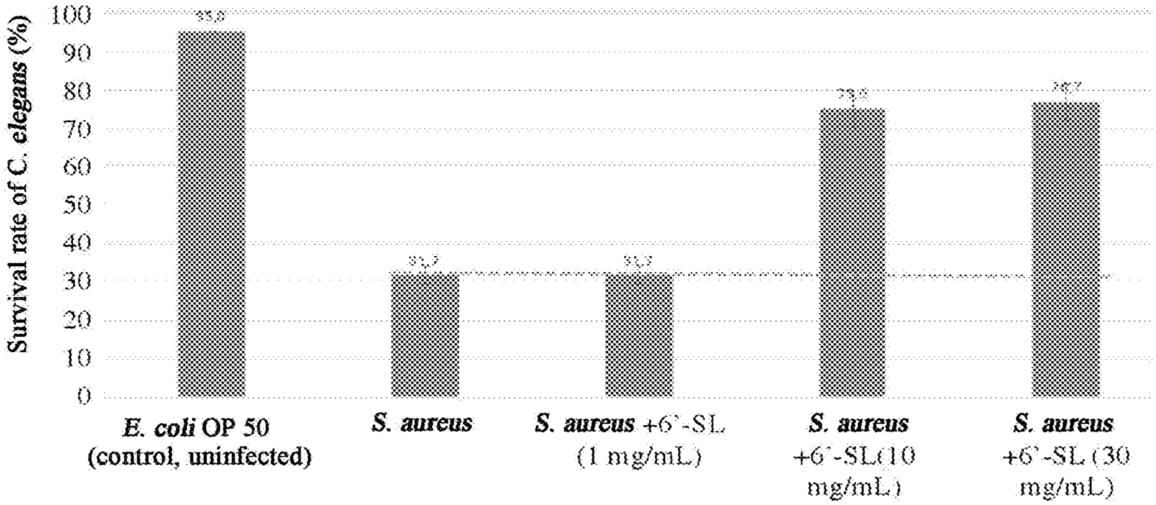
FIG. 10 shows the effect of several different doses of the human milk oligosaccharide 6'-SL on the survival rate of *C. elegans* on the third day of infection by *Staphylococcus aureus*.

Example 4. Effects of Different Concentrations of the Human Milk Oligosaccharide 6'-SL on the Survival Rate of Nematodes after *Staphylococcus aureus* Infection As shown in FIG. 9, a similar effect was also observed in 6'-SL:when 6'-SL was added at a concentration of 1 mg/mL, the survival rate of *Caenorhabditis elegans* (in short, nematodes) after *Staphylococcus aureus* (in short, *S. aureus*) infection was not greatly improved, but when 6'-SL was added at a concentration of 10 mg/mL or 30 mg/mL, the survival rate of nematodes after infection with *S. aureus* was significantly improved. Seen as such, 6'-SL also has a dose-effect relationship in the regulation of nematode growth after *Staphylococcus aureus* infection. The histogram in FIG. 10 shows the different effects of different doses of 6'-SL on the survival rate of nematodes after being infected by *Staphylococcus aureus* for 3 days, showing that the protective effect is more pronounced at higher concentrations. Also, the survival rate with 6'-SL at 10 mg/mL was similar to that at 30 mg/mL, and compared with other tested HMOs alone, it was found that the survival rate of nematodes under the protection of 6'-SL was higher, up to 75%. It was deducted that 6'-SL at lower than 10 mg/mL had a potential to have a notably better protection for nematode survival in the presence of *Staphylococcus aureus* infection than that of the negative control group.

Figure 11:
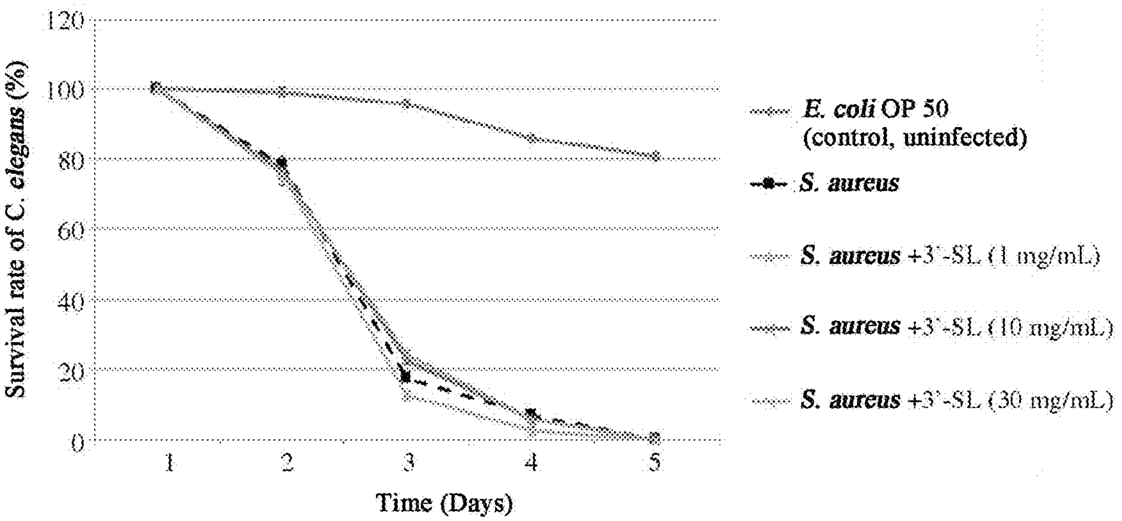
FIG. 11 shows the effect of different doses of the human milk oligosaccharide 3'-SL on the survival rate of *C. elegans* when infected by *Staphylococcus aureus*. The interventions (HMOs) added during the infection phase were the same for each group in the figure as for the culture phase, respectively.
Figure 12:
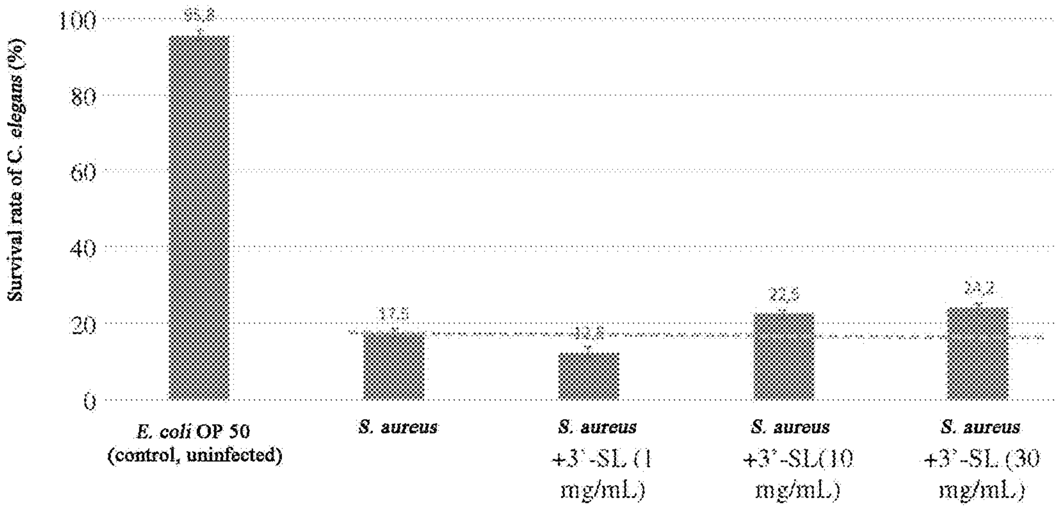
FIG. 12 shows the effect of different doses of the human milk oligosaccharide 3'-SL on the survival rate of *C. elegans* on the third day of infection by *Staphylococcus aureus*.

In addition, three concentrations (1 mg/mL, 10 mg/mL and 30 mg/mL) were also tested in the same way for the 6'-SL isomer, 3'-SL, but no significant effect was observed (FIG. 11, FIG. 12). Thus, the response to *Staphylococcus aureus* infection is affected by the specific structure of the material, and not all oligosaccharide materials can be effective, while different materials may also have different effects.

Example 5. Effects of Different Concentrations of Human Milk Oligosaccharide Compositions on the Survival Rate of *Caenorhabditis elegans* after *Staphylococcus aureus*

Infection, and Comparison with the Same Dose of the $_{individual}$ HMOs

Figure 13:
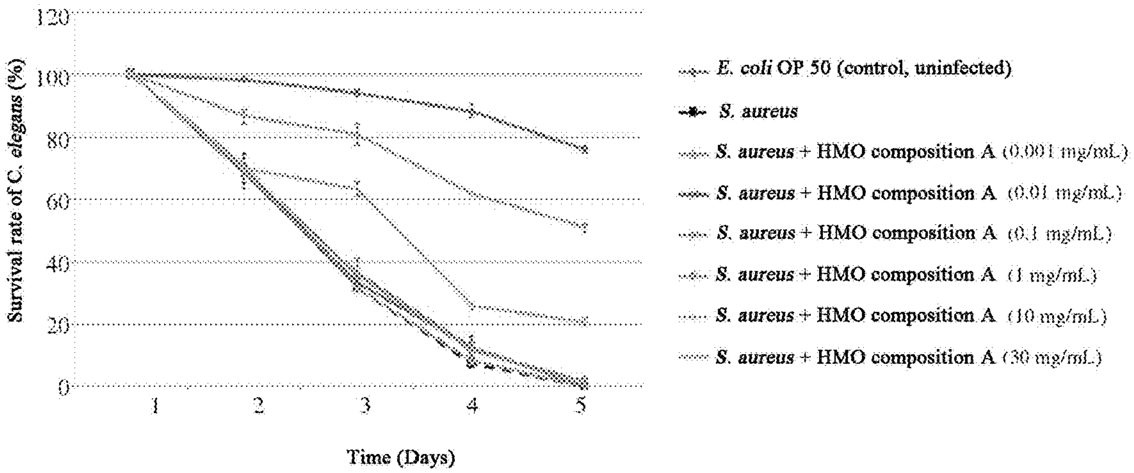
FIG. 13 shows the effect of different doses of the human milk oligosaccharide compositions on the survival rate of *C. elegans* when infected by *Staphylococcus aureus*. The interventions (HMOs) added during the infection phase were the same for each group in the figure as for the culture phase, respectively.
Figure 14:
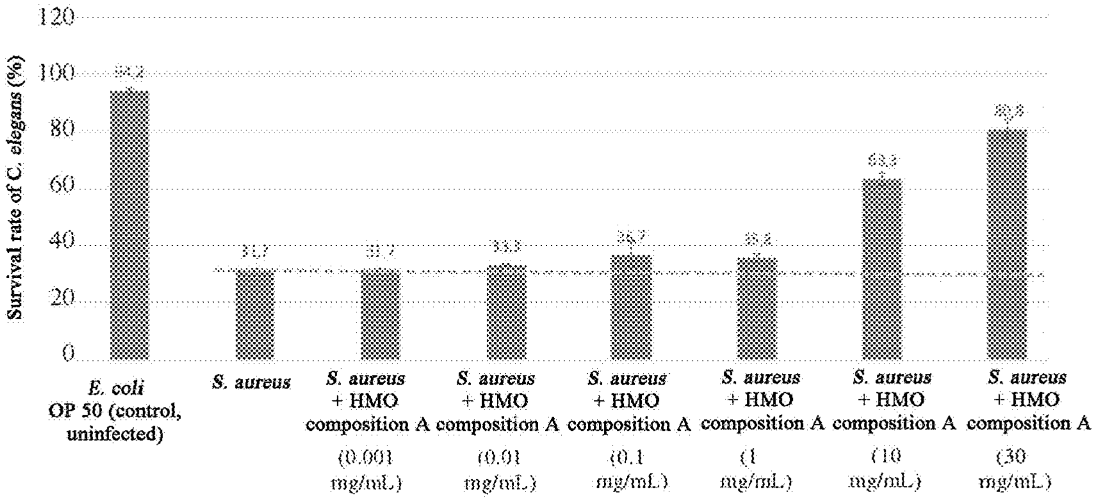
FIG. 14 shows the effect of different doses of the human milk oligosaccharide compositions on the survival rate of *C. elegans* on the third day of infection by *Staphylococcus aureus*.

First, to determine the dose range of the HMO composition tested in the experiment, six different doses of the HMO Composition A were tested. As shown in FIG. 13, doses at 1 mg/mL or less did not show any effect, while 10 mg/mL caused a considerable increase in nematode survival rate with a significant effect (P<0.0001). Therefore, as shown in FIG. 13, higher doses were tested, and when the dose of HMO Composition A reached 30 mg/mL, the protective effect was significantly increased, and the effect was significant (P<0.0001). Seen as such, the HMO Composition A had a significant protective effect against *Staphylococcus aureus*, which was dose-dependent and more desirable at 10 mg/mL and 30 mg/mL. The histogram in FIG. 14 shows the different effects of different doses of the HMO Composition A on the survival rate of nematodes after being infected by *Staphylococcus aureus* for 3 days, showing that the protective effect is more pronounced at higher concentrations.

Figure 15:
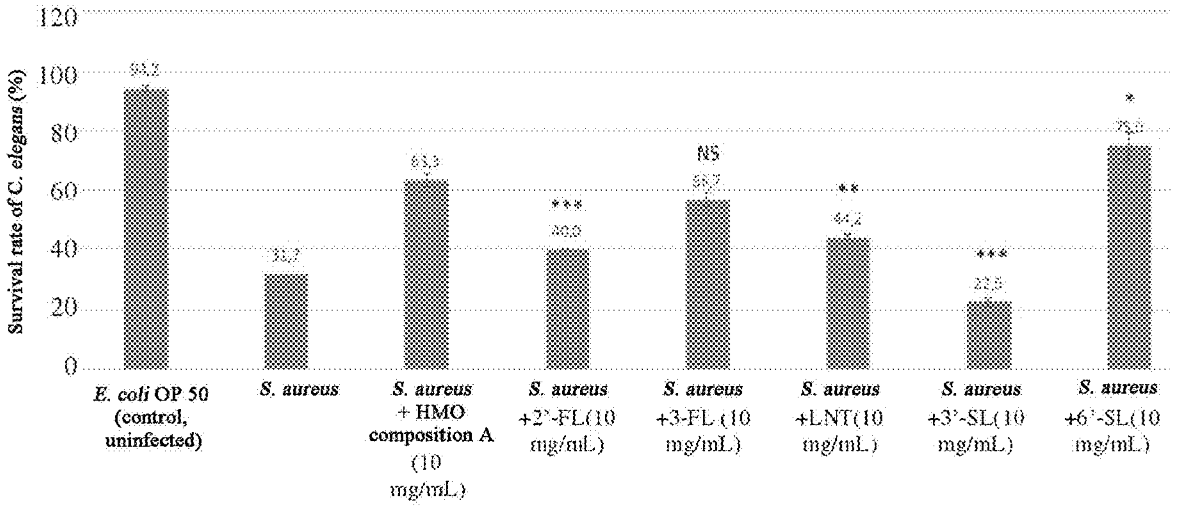
FIG. 15 shows a comparison of the different effects of 10 mg/mL of the human milk oligosaccharide composition and each of the five human milk oligosaccharides alone on the survival rate of *C. elegans* on the third day of infection by *Staphylococcus aureus*.
Figure 16:
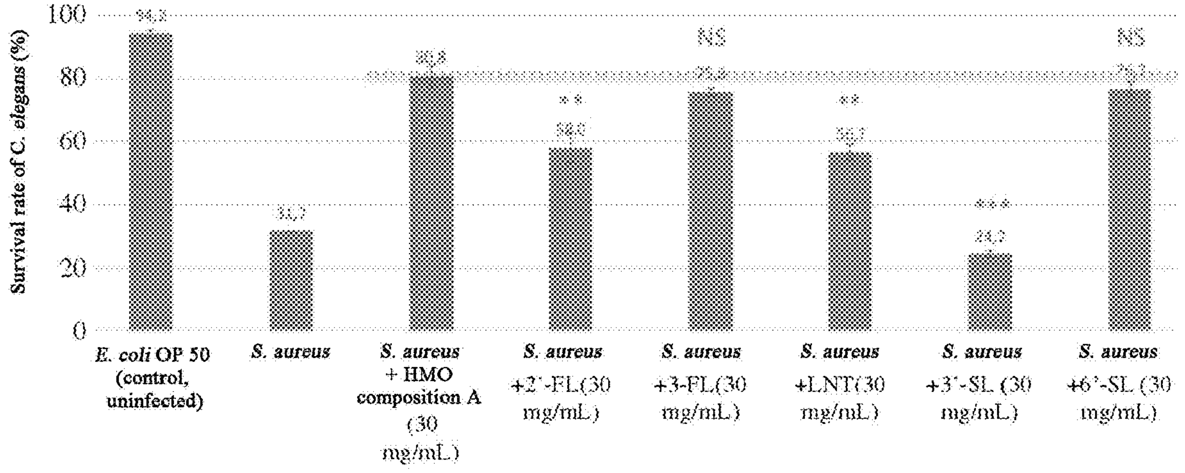
FIG. 16 shows a comparison of the different effects of 30 mg/mL of the human milk oligosaccharide composition and each of the five human milk oligosaccharides alone on the survival rate of *C. elegans* on the third day of infection by *Staphylococcus aureus*.

In addition, on the third day of culture with *Staphylococcus aureus*, the human milk oligosaccharides composition A was compared with each HMO at doses of 10 mg/mL (FIG. 15) and 30 mg/mL (FIG. 16), and it was found that at 10 mg/mL, the effect of the human milk oligosaccharides composition A was better than that of the HMOs such as 2'-FL, LNT and 3'-SL alone at the same dose, which was significant. At 30 mg/mL, the effect of the human milk oligosaccharide composition A was better than that of the HMOs such as 2'-FL, LNT and 3'-SL alone at the same dose, which was significant, and had a tendency to be better than that of 3-FL and 6'-SL alone, showing a synergistic effect to a certain extent.

Figure 17:
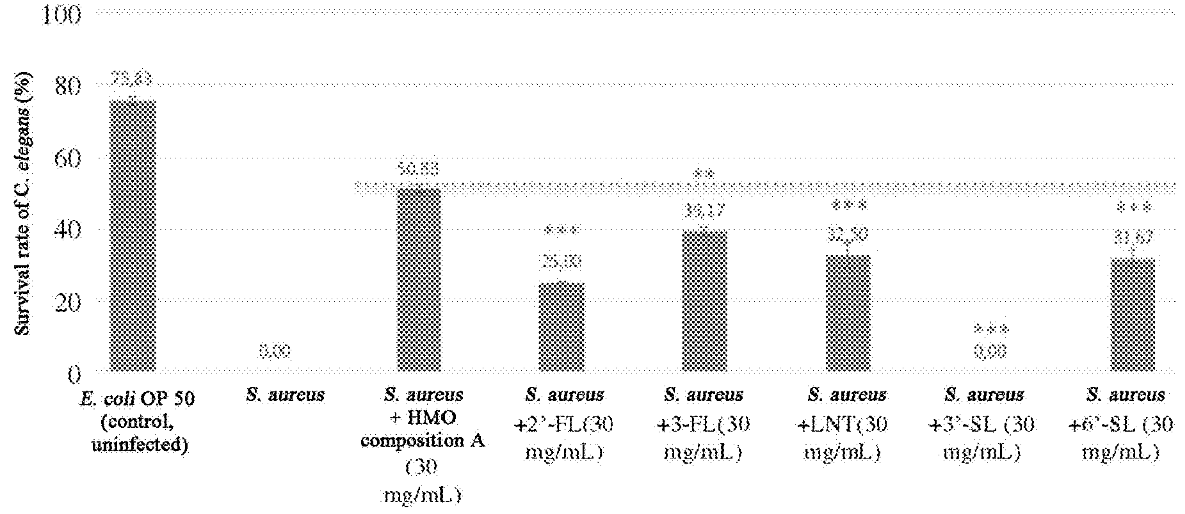
FIG. 17 shows a comparison of the different effects of 30 mg/mL of the human milk oligosaccharide composition and each of the five human milk oligosaccharides alone on the survival rate of *C. elegans* on the fifth day of infection by *Staphylococcus aureus*.

On the fifth day of culture with *Staphylococcus aureus*, the human milk oligosaccharide composition A was compared with each HMO again at a dose of 30 mg/mL (FIG. 17), and the effect of the human milk oligosaccharide composition was better than that of all the tested HMOs, including 2'-FL, 3-FL, LNT, 3'-SL and 6'-SL, alone at the same dose, which was significant and demonstrated a synergistic effect and advantage of the composition.

Figure 18:
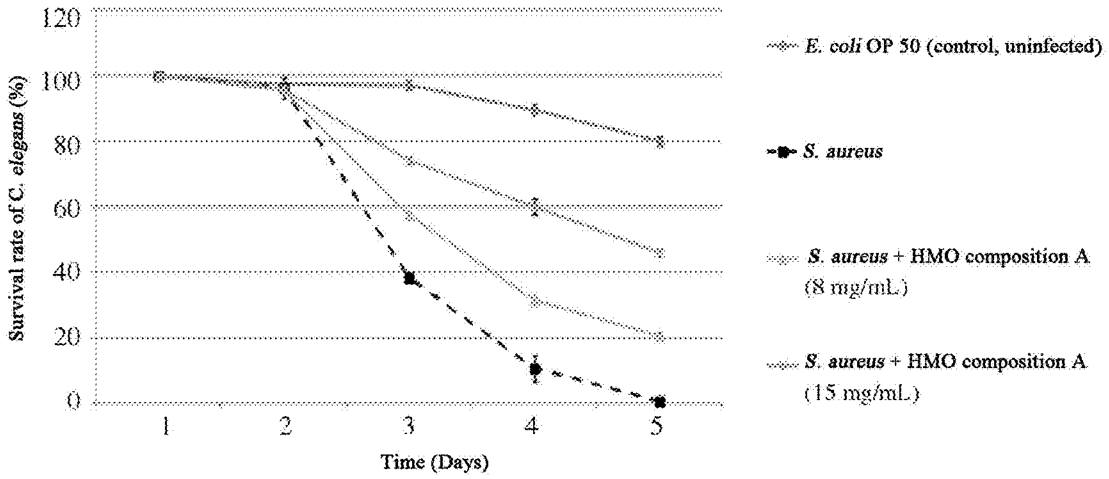
FIG. 18: pathogenic bacteria survival test using *Staphylococcus aureus* in the nematode model with composition A tested at concentrations of 8 and 15 mg/mL. The interventions (HMOs) added during the infection phase were the same for each group in the figure as for the culture phase, respectively.

In another batch of experiments of the present invention, the HMO composition A was also evaluated for the improvement of the survival rate of nematodes after infection by *Staphylococcus aureus* at a concentration of 8 mg/mL and 15 mg/mL, with the results shown in FIG. 18. It could be seen that at the concentration of 8 mg/mL (P<0.001) and 15 mg/mL (P<0.0001), the composition A could improve the survival rate of nematodes, showing a protective effect against *Staphylococcus aureus* infection. Comparison of the protective effects of both concentrations indicated that the protective effect was higher at the concentration of 15 mg/mL (P<0.001). Seen as such, a dose-effect response of the composition was observed at this ratio.

Figure 19:
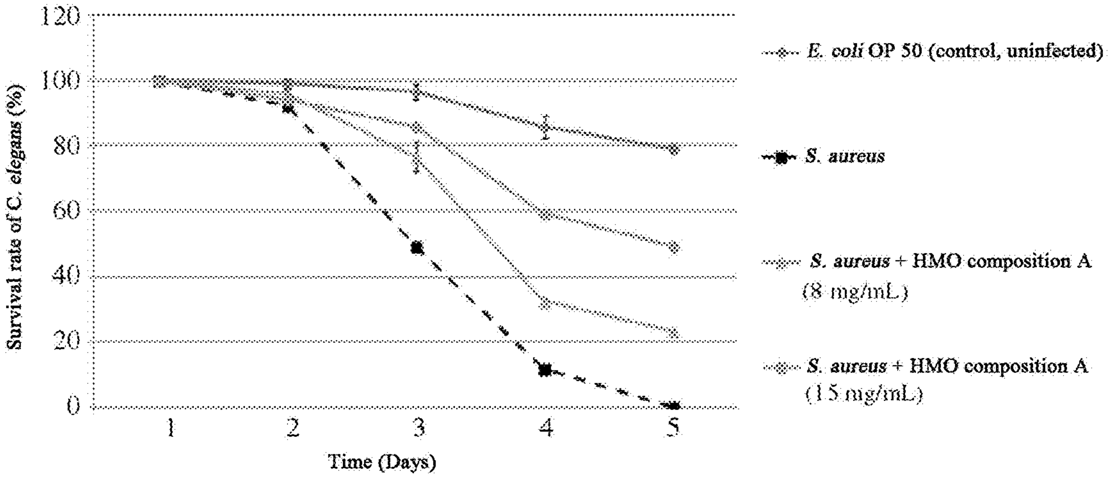
FIG. 19: pathogenic bacteria survival test using *Staphylococcus aureus* in the nematode model with the composition G tested at concentrations of 8 and 15 mg/mL. The interventions (HMOs) added during the infection phase were the same for each group in the figure as for the culture phase, respectively.

Likewise, the HMO composition G was compared at two different concentrations, with the results shown in FIG. 19. It was found that at a concentration of 15 mg/mL, the HMO composition had a stronger protective effect on nematode survival under *Staphylococcus aureus* infection (P<0.0001). At a concentration of 8 mg/mL, the composition G also showed a significant protective effect (P<0.0001) compared to the control without any test substance added. Seen as such, a dose-effect response of the composition was observed at this ratio.

Figure 20:
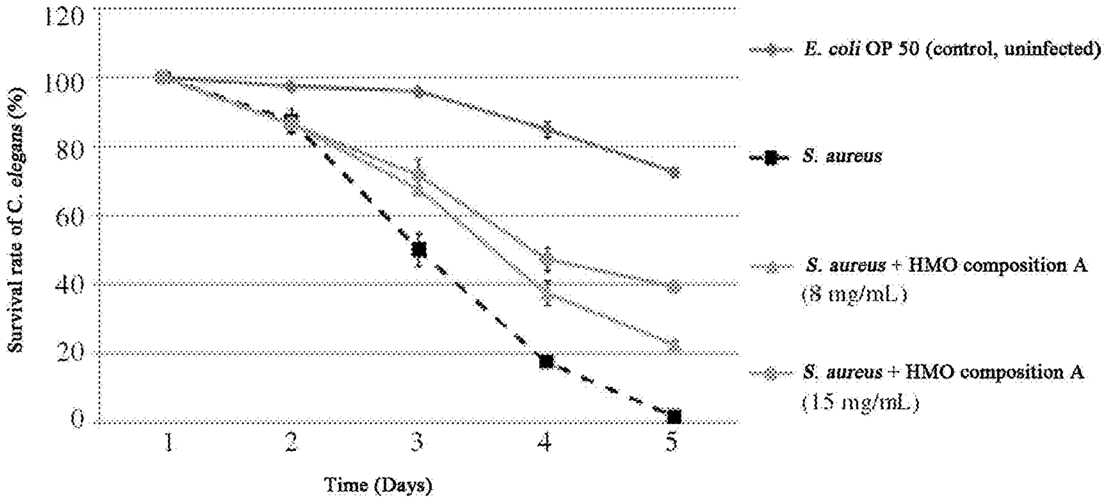
FIG. 20: pathogenic bacteria survival test using *Staphylococcus aureus* in the nematode model with the composition H tested at concentrations of 8 and 15 mg/mL. The interventions (HMOs) added during the infection phase were the same for each group in the figure as for the culture phase, respectively.

FIG. 20 presents nematode survival curves of the HMO composition H at two different concentrations. It can be seen that both concentrations of 8 mg/mL (P<0.001) and 15 mg/mL (P<0.0001) have significantly higher survival rates than the control group without the test substance, in which the protective effect of the HMO composition H at 15 mg/mL is slightly higher than that at 8 mg/mL (P<0.05). Seen as such, a dose-effect response of the composition was observed at this ratio.

Figure 21:
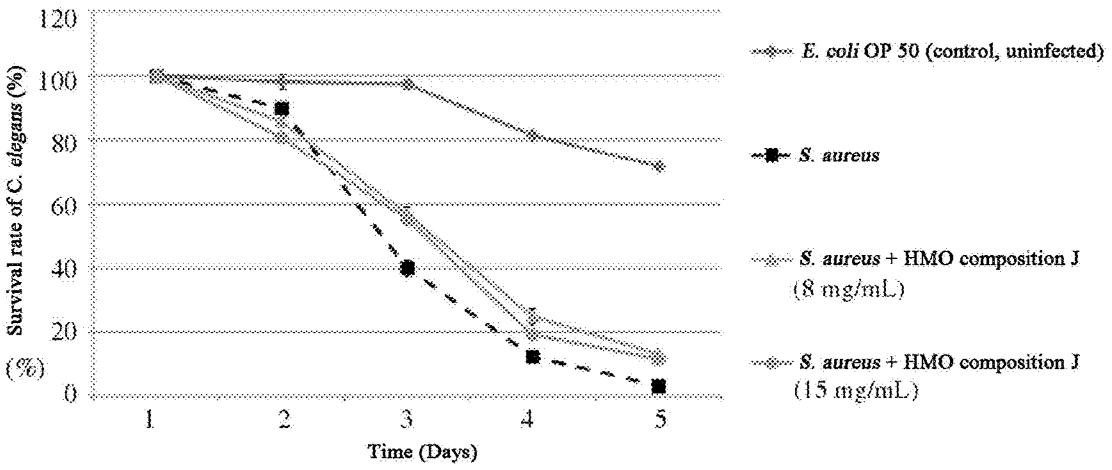
FIG. 21: pathogenic bacteria survival test using *Staphylococcus aureus* in the nematode model with the composition J tested at concentrations of 8 and 15 mg/mL. The interventions (HMOs) added during the infection phase were the same for each group in the figure as for the culture phase, respectively.

Also evaluated in the present invention was the effect of the HMO Composition J. As shown in FIG. 21, both concentrations of 8 mg/mL (P<0.01) and 15 mg/mL (P<0.05) slightly improve the survival rate compared to the control group without the test substance, and there is no difference in the survival-improving effect between the two concentrations (P>0.05). Seen as such, no dose-effect response of the composition was observed at this ratio.

Figure 22:
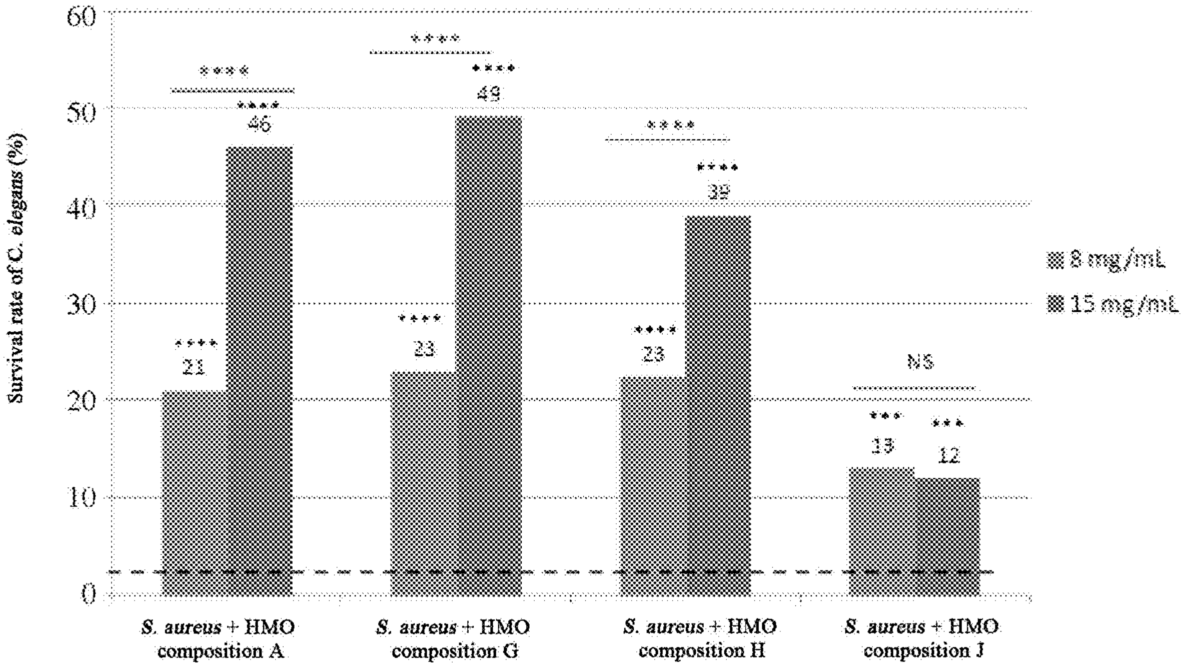
FIG. 22: percentage of nematode survival after 5 days of infection. Nematodes were co-cultured with the HMO compositions A, G, H, J at different doses (8 and 15 mg/mL). The dotted line shows nematode survival in the absence of any interventions upon *Staphylococcus aureus* infection. The asterisks represent the statistical differences between the test groups and the *S. aureus* control group (no intervention).

The protective effects of the tested HMO compositions at various ratios on the survival rate of nematodes under *Staphylococcus aureus* infection were compared, with the results shown in FIG. 22. It was found that on the fifth day post-infection, a protective effect on the nematode survival was shown at all ratios. Among them, the HMO composition A and composition G, both under the condition of 15 mg/mL, showed the highest protective effect (P<0.0001). In addition, the HMO composition G at 15 mg/mL also resulted in higher nematode survival on the fifth day after infection (P<0.0001). Almost all the groups tested had lower protection at 8 mg/mL than that at 15 mg/mL, except for the HMO Composition J. The protective effect of HMO composition J on nematode survival was the lowest at both doses, and there was no difference between the doses (P>0.05).

As such, the HMO composition A, the HMO composition G, and the HMO composition H all showed a good dose-effect response, that is, the protective effect at a higher concentration was significantly better than that of a lower concentration. However, the HMO composition J did not show a dose-effect response, that is, there was no difference in the protective effect between higher and lower concentrations. Also, compared with the negative control, the effect of the HMO composition J was inferior on improving the survival rate than those of the HMO composition A, the HMO composition G and the HMO composition H at different ratios.

Example 6. Disc Diffusion Bacteriostatic Zone Experiment

In order to determine whether the tested materials themselves have an antibacterial effect, a bacteriostatic zone experiment for disk diffusion was carried out. Discs were prepared with sterile filter paper impregnated with the tested HMO materials (10 mg/mL, 30 mg/mL), and the discs were dried overnight under sterile conditions. *Staphylococcus aureus* ATCC25923 ($1.0\times10^6$CFU/mL) was spread evenly on the surface of a NGM agar plate, and then the discs were placed on the surface of the inoculated agar plate petri dish. Gentamicin (200 μg/mL) was used as a positive control. All dishes were incubated at 37° C. for 18 hours. Whether the test materials can directly inhibit bacterial growth or has antibacterial activity was confirmed by observing whether a transparent annular ring was formed around the disc.

Figure 23:
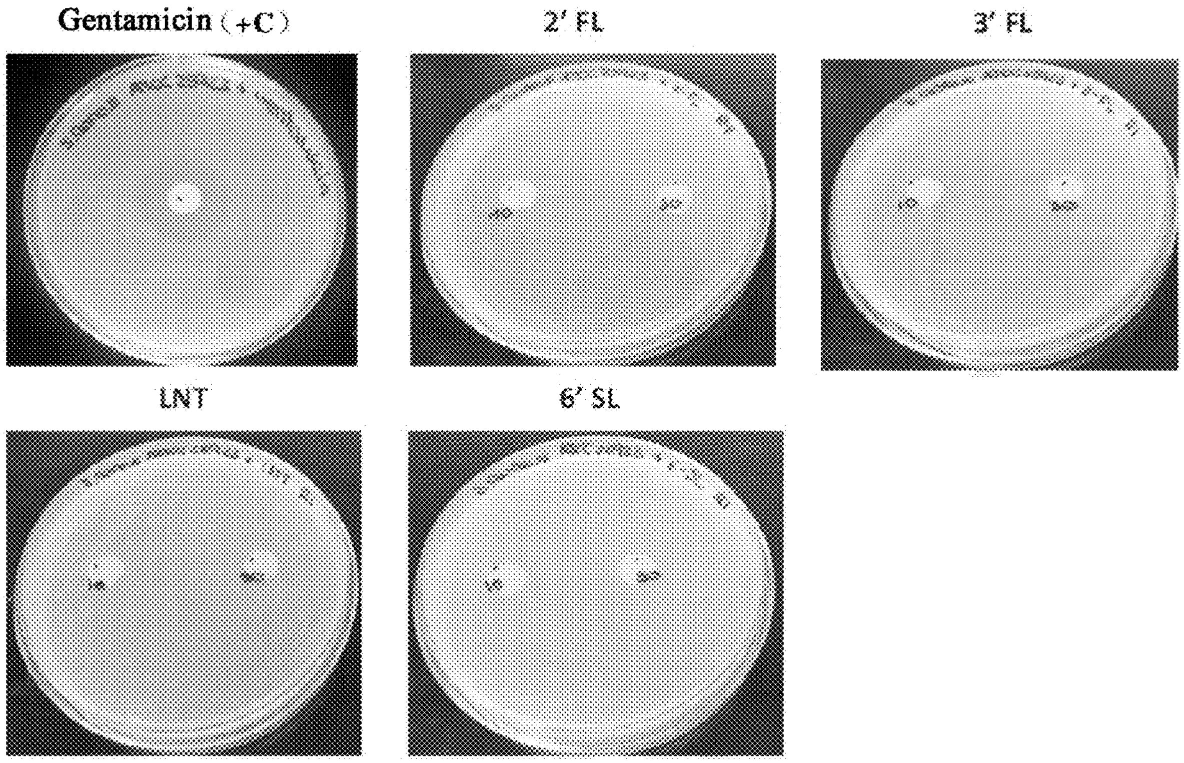
FIG. 23 shows the observation of the presence or absence of a direct bacteria inhibition of the various human milk oligosaccharides alone co-cultured with *Staphylococcus aureus* in a Petri dish disc diffusion test and the comparison with the positive control gentamicin.

FIG. 23 shows the observation of the presence or absence of a direct bacteria inhibition of the various human milk oligosaccharides alone co-cultured with *Staphylococcus aureus* in a Petri dish disc diffusion test and the comparison with the positive control gentamicin.

In order to investigate whether the protective effects of individual HMOs or their compositions against *Staphylococcus aureus* infection, as presented in previous tests, were derived from direct bactericidal or bacteriostatic function, a test was carried out in which the test material was incubated with the bacteria population and observed whether an bacteriostatic zone of was formed. As shown in the figure, at two different concentration (left: 10 mg/mL, right: 30 mg/mL), none of the human milk oligosaccharides alone formed a transparent annular bacteriostatic zone around the inoculation site. The positive control, gentamicin, showed a bacteriostatic effect, which was marked by the formation of a transparent annular bacteriostatic zone. Seen as such, the protective effects of each individual human milk oligosaccharide and the compositions thereof in this study on nematode against *Staphylococcus aureus* infection are not resulted from the direct bactericidal function of the materials, but a possible underlying mechanism by improving the resistance of the organism against *S. aureus* infection, such as activating the innate immune system of the organism, which in turn plays a role in the resistance and protection against bacteria.

Described above are only preferred embodiments of the present invention, which are not intended to limit the present invention. Any modification, equivalent replacement, improvement and the like made within the spirit and principle of the present invention shall be included within the protection scope of the present invention.

The invention claimed is:

1. A method for treating a disease associated with *Staphylococcus aureus* infection in an individual which has been infected with *Staphylococcus aureus*, comprising administering to a subject an effective amount of a human milk oligosaccharide consisting of 2'-fucosyllactose (2'-FL), 3-fucosyllactose (3-FL), lacto-N-tetraose (LNT), 3'-sialyllactose (3'-SL), and 6'-sialyllactose (6'-SL), with a ratio of the human milk oligosaccharides of 2'-FL: 3-FL: LNT: 3'-SL: 6'-SL=53%: 21%: 16%: 5%: 5%; wherein the effective amount is 30 mg/mL.

2. The method according to claim 1, which is characterized by one or more of the following:

(1) the human milk oligosaccharide is administered at a dose of 0.012 to 12 g/day;

(2) the disease er discomfort associated with Staphylococcus aureus infection is selected from food poisoning, enteritis, pneumonia, skin infection, wound ulceration, and meningitis; and (3) the individual is an infant, a toddler, a child, or an adult.

* * * * *